United States Patent [19]

Mikhail

[11] Patent Number: 5,236,462
[45] Date of Patent: Aug. 17, 1993

[54] METAL-BACKED PATELLAR PROSTHESIS

[76] Inventor: W. E. Michael Mikhail, 4203 Shamley Green, Toledo, Ohio 43623

[21] Appl. No.: 689,500

[22] Filed: Apr. 23, 1991

[51] Int. Cl.$^5$ .............................................. A61F 2/38
[52] U.S. Cl. ..................................................... 623/20
[58] Field of Search ........................ 623/16, 18, 20, 66

[56] References Cited

U.S. PATENT DOCUMENTS

| | | |
|---|---|---|
| 3,765,033 | 10/1973 | Goldberg et al. |
| 3,878,566 | 4/1975 | Bechtol |
| 4,081,866 | 4/1978 | Upshaw et al. |
| 4,158,894 | 6/1979 | Worrell |
| 4,462,120 | 7/1984 | Rambert et al. |
| 4,479,271 | 10/1984 | Bolesky et al. ........................ 623/20 |
| 4,778,473 | 10/1988 | Matthews et al. ..................... 623/20 |
| 4,822,366 | 4/1989 | Bolesky |
| 4,944,756 | 7/1990 | Kenna ................................... 623/20 |

FOREIGN PATENT DOCUMENTS

0719625  3/1980  U.S.S.R. ................................ 623/20

OTHER PUBLICATIONS

Catalog of Dow Corning Wright, Arlington, Tenn., copyright 1989 entitled, "Whiteside ORTHOLOC® Modular Knee System".
Catalog of Intermedics Orthopedics, Inc., Austin, Tex., copyright 1987 entitled "The Intermedics Natural-Knee® System with Cancellous-Structured Titanium TM".
Catalog of DePuy, Warsaw, Ind., division of Boehringer Mannheim Corporation, copyright 1988, entitled "The AMK TM Total Knee System-Design Rationale and Surgical Procedure", pp. 13 and 47.
Catalog of Biomet, Inc., Warsaw, Ind., entitled "AGC Total Knee System—Patellar Femoral Systems".
Booklet published by Smith & Nephew Richards, Inc., Memphis, Tenn., entitled "Surgical Technique-Genesis TM Total Knee System Posterior-Stabilized" Article entitled Patellar Prosthesis Positioning in Total Knee Arthroplasty by Luis S. J. Gomes, M. D., Joan E. Bechtold, Ph.D. and Romon B. Gustilo, M.D., published at pp. 72-81 of the Nov., 1988 issue of Clinical Orthopaedics and Related Research.
Catalog of Johnson & Johnson Orthopaedics, New Brunswick, N.J. entitled, "P.F.C.® Total Knee System".

*Primary Examiner*—David Isabella
*Attorney, Agent, or Firm*—Emch, Schaffer Schaub & Porcello Co.

[57] ABSTRACT

A two-piece patellar prosthesis for use in combination with a prepared patella has a plastic component with a dome, a body portion and a central post and a second metal component engaged to the surface of the first component opposing said dome, said second component having a porous surface to promote bone ingrowth and a plurality of spikes for preventing rotation.

14 Claims, 3 Drawing Sheets

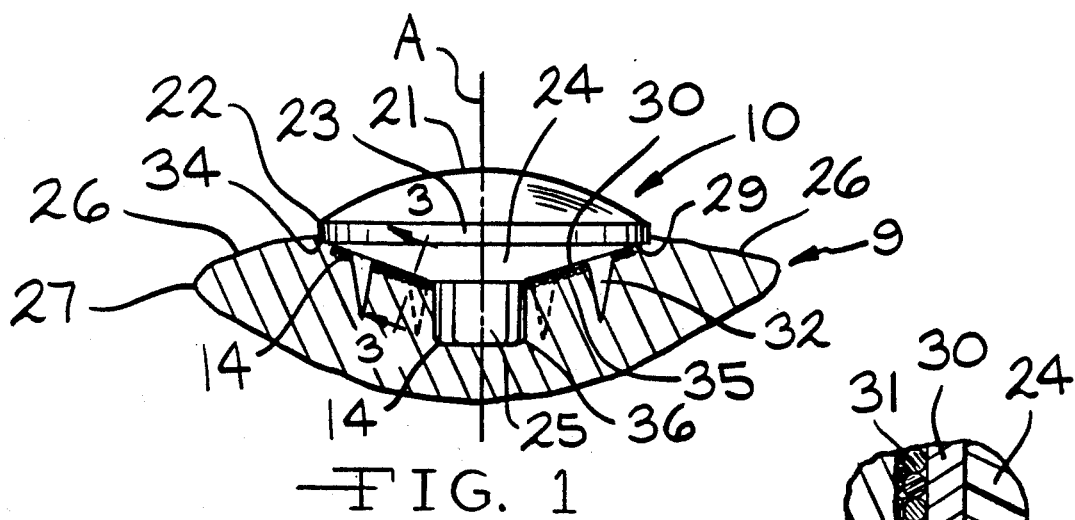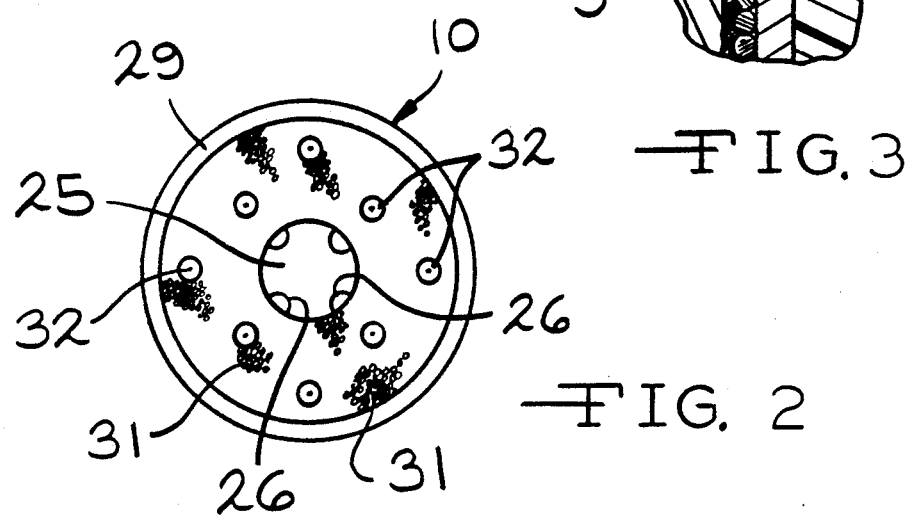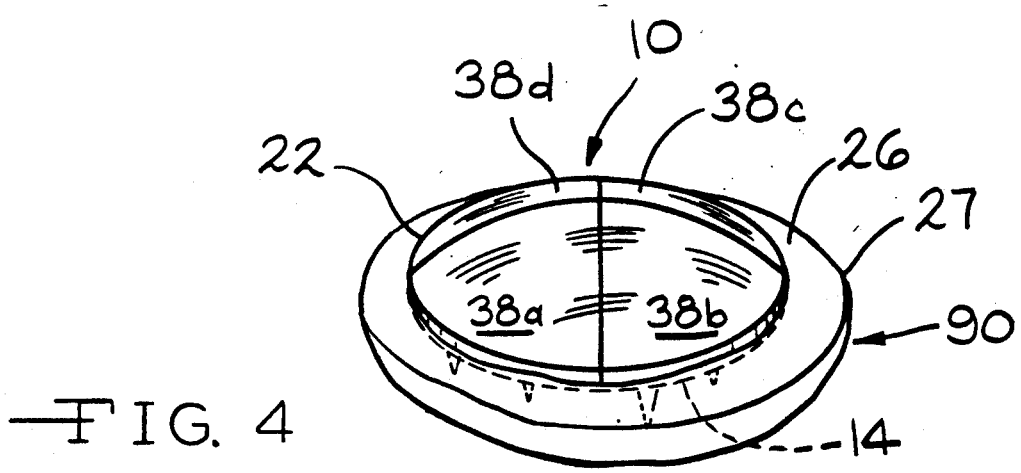

METAL-BACKED PATELLAR PROSTHESIS

TECHNICAL FIELD

The present invention relates to a patellar prosthesis for use with a total knee system and more specifically to a non-cemented prosthesis having a domed component formed of plastic and a metal backing component having a beaded or porous surface to promote ingrowth of bone tissue and spikes to prevent rotation following implantation.

BACKGROUND ART

In total knee arthroplasty it is customary to resurface the articulating ends of the femur and the tibia with prostheses which are fastened to the cut and prepared ends of the femur and tibia. One such prosthesis is that described in a catalog published by Johnson & Johnson Orthopaedics Inc. entitled "P.F.C. Total Knee System" ("P.F.C. is a registered trademark of Johnson & Johnson Orthopaedics Inc.) using a surgical technique described in a booklet published by Johnson & Johnson Orthopaedics Inc., entitled "The F.P.C. Total Knee System with Specialist Instruments—Surgical Technique" and another published by Johnson & Johnson Orthopaedics Inc. entitled "Patellar Resurfacing with Specialist ®Instruments in Total Knee Arthroplasty-Surgical Technique." Another such prosthesis is described in U.S. Pat. No. 4,822,366.

One component of the P.F.C. Total Knee System and virtually every other total knee replacement system utilized is a patellar component.

Heretofore great difficulty has been encountered in providing a patellar component prosthesis which will endure, for extended periods of time, the rigors to which such components are placed. Thus, a patellar component is subjected to continual rubbing against the femoral component of the total knee system with each flexing movement of the leg. As a result, the patellar component may wear to such an extent as to impede function of the knee even though the other components may not be worn out. In addition, it may also cause undue wear on the other components of a total knee system.

In a total knee system, the patellar component is typically a dome-shaped member which is implanted on a flat surface or a recess cut into the patient's patella. The patellar implant may either be all plastic, typically high molecular weight polyethylene (HMWPE) or plastic with a metal backing formed of titanium, chrome-cobalt alloy, stainless steel or the like.

In addition to the patellar implant shown in the Johnson & Johnson Orthopaedics brochure entitled "P.F.C. Total Knee System", other types of patellar implants are disclosed in catalogs published by Dow Corning Wright entitled "Whiteside Ortholoc Modular Knee System" and published by DePuy, Warsaw, Ind., a Division of Boehringer Mannheim Corporation, entitled "The AMK Total Knee System."

As will be appreciated, it is desirable to utilize a patellar implant which combines the advantages of requiring a minimal amount of cutting of the patella, secure placement of the patellar implant and the ability to easily remove such implant in the event revision is required.

Accordingly, it is an object of the present invention to provide a patellar prosthesis for use in combination with the prepared patella bed in which a minimal amount of the patient's natural patella is required to be removed.

It is a further object of the present invention to provide a patellar prosthesis designed for implantation in a patella which can be replaced with minimal damage to the patella in the event revision is required.

It is an additional object of the present invention to provide a metal-backed patellar prosthesis suitable for implantation without the cement.

DISCLOSURE OF INVENTION

The present invention relates to a new and improved patellar prosthesis which may be implanted without the use of cement and which is formed of a first plastic component having a domed portion intended to face outwardly from the patella for engagement with the condylar or trochlear groove of a femoral prosthesis component. The first component includes a body portion and a central post extending from said body portion in a direction away from the domed portion and intended to be positioned in a recess cut into the patella below a cavity reamed therein to receive the body portion. Preferably the lower surface of the body portion opposite the domed portion has a conical or other downwardly tapering shape as it approaches the central post to provide increased thickness at the center over that resulting from the domed surface itself. The second component is formed of metal and frictionally or adhesively engaged to said plastic component on its surface opposite the domed portion. The second component encircles the central post, has a beaded section or porous coating intended to engage the prepared portion of the patella intended to receive bone growth and has a plurality of spikes extending therefrom for placement and retention in the patella. The surface of the second metallic component is tapered as it approaches the central post.

BRIEF DESCRIPTION OF THE DRAWINGS

FIG. 1 is an elevational view partly in section showing the patellar prosthesis of the present invention implanted in a patella.

FIG. 2 is a plan view showing the lower side of the patellar prosthesis intended to face inwardly toward the prepared patella.

FIG. 3 is a sectional view taken through line 3—3 of FIG. 1.

FIGS. 4–7 are schematic views showing the procedure for removing the patellar prosthesis of the present invention in the event resection is required.

BEST MODE OF CARRYING OUT INVENTION

Figure 5:
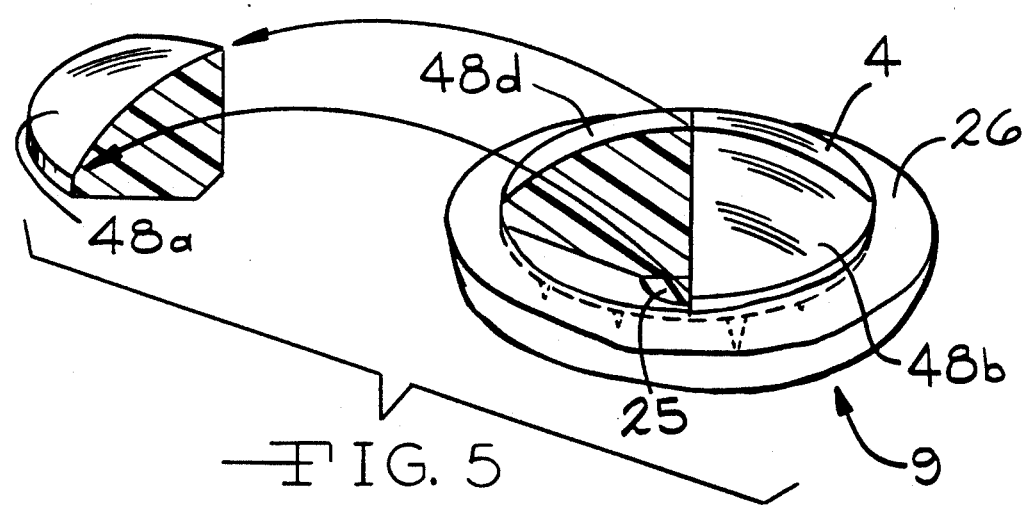

Application Ser. No. 07/599,432 filed Oct. 18, 1990 by the Applicant herein (incorporated herein by reference) as a continuation-in-part to application Ser. No. 07/503,088 filed Apr. 11, 1990 discloses a patellar prosthesis requiring minimal amount of bone removal but intended for implantation using bone cement. The patellar prosthesis of the present invention also requires only a minimal amount of bone removal but is specifically tailored for use in those situations in which the surgeon elects not to use bone cement or for other reasons believes it more suitable under the circumstances of the particular patient.

Referring now to the drawings, there is shown in FIG. 1 a human patella 9 and a patellar prosthesis 10 of the present invention implanted therein. The patellar prosthesis 10 of the present invention is intended to be used as part of a total knee system used in total knee replacement and which includes a femoral implant, a tibial base implant and a tibial insert. Typically, the femoral implant and tibial base implant are formed of metal such as titanium alloy or cobalt-chrome while the tibial insert is formed of plastic such as high molecular weight polyethylene.

Referring to FIG. 1, the patella 9, prior to osteotomy to prepare it to receive the patellar prosthesis 10, included a natural dome extending to an apex at the central portion thereof. As previously discussed, it is desirable that only minimal portions of the patella be removed in preparing the patella 9 to receive the prosthesis 10. Thus, as shown in FIG. 1, the patella 9 has been prepared by reaming or otherwise to form a cavity 14 while leaving intact an annular outer portion 26 of such dome extending from the cavity 14 to the peripheral edge 27. Some patellar prosthesis implant procedures require that the entire portion of the natural dome of the patella 9 be removed completely to the peripheral edge 27. Others require that only the central portion of the dome be removed thus leaving an outer peripheral portion 26 of the natural dome. A major advantage of the patellar prosthesis 10 of the present invention is that it may be implanted with a minimal amount of bone removed from the patella so that outer peripheral portions 26 will remain intact. Another advantage of the present invention resides in the fact that it may be readily removed in the event resectioning is required and replacement with a new patellar prosthesis is desired.

The patellar prosthesis 10 of the present invention includes two components, namely, a first component 11 preferably formed of a plastic material such as high molecular weight polyethylene and a second component 12 formed of metal such as titanium or a cobalt chrome alloy. The first component 11 includes a dome 21 which preferably is convex throughout extending to a peripheral edge 22 which, upon implantation will meet smoothly with the outer portion 26 of the dome of the patella 9 or, preferably, may extend above it 1-2 mm in order to allow for subsidence of the patellar implant 10 in the patella 9. Extending downwardly from the peripheral edge 22 in a direction away from the dome 21 is a short cylindrical body section 23. Extending downwardly and inwardly toward the longitudinal axis is a conical-shaped body portion 24 from which a central post 25 extends. Preferably, the post 25 has a plurality of longitudinal grooves 26.

The second component 12 of the patellar prosthesis 10 is formed of metal and includes a shell 30 snugly engaging the lower tapered, conical face of the body portion 24 of the first component. The metallic shell 30 encircles the central post 25 and may be retained to the first component 11 as a result of an interference fit therewith. For example, such second metallic component 12 may snugly engage the central post 25. A suitable adhesive may also be used to retain such second component to the lower surface of the conical-shaped body portion 24. As may be seen particularly in FIGS. 1 and 2, the second metallic component 12 does not extend to the outer peripheral edge of the body portion defined by the juncture of the lower surface of the conical-shaped body portion 24 with the surface of the short cylindrical body section 23 but rather is spaced therefrom to leave an annular ring 29 of the lower surface of the conical-shaped body portion 24 exposed to contact the outer surface of the cavity of the prepared patella 9. The purpose of providing the annular ring 29 of exposed plastic of the lower surface of the conical-shaped body portion 24 is to keep the second metallic component 12 spaced from the edge of the cavity 14 in order to keep any metal debris which may develop over time contained within the cavity 14 and, thus, prevent it from being released to contaminate the femoral component or otherwise interfere with the operation of the total knee system.

The portion of the second metallic component facing away from the conical-shaped body portion 24 has affixed thereto by sintering or other means well-known in the art of joint prostheses manufacture a series of beads 31 forming a porous surface intended to receive bone ingrowth for retaining the patellar prosthesis 10 in the cavity 14 formed in the patella 9. Porous metal surfaces having structures of the types produced by Astro Met, Inc., Cincinnati, Ohio and marketed under the name "Astro Met" may also be used as the surface for promoting bone ingrowth. U.S. Pat. No. 4,164,794 discloses a prosthetic device having a sintered porous coating of selected bioengineering thermoplastics which could be used for such porous surface. The second metallic component also has a series of spikes 32 extending between the beads 31. There may be any reasonable number of spikes 32 but preferably, there will be 3 to 8 spikes 32. The spikes 32 will be 3-6 millimeters in length and will taper to a point from a base of approximately 2 millimeters in diameter. The respective centerlines of the spikes 32 are parallel to the axis A. Preferably, some of the spikes 32 are closer to the longitudinal axis A of the post 25 than others. The spikes 32 are intended to be driven into the patella 9 and function to prevent rotation of the patellar prosthesis 10 following implantation. Depending upon the hardness of the patella 9, it may be necessary to drill lead-in passages for receiving such spikes 32.

In the osteotomy to prepare the patella 9 to receive the patellar prosthesis of the present invention, the patella has drilled and reamed therein the cavity 14 which includes a first cylindrical-shaped section 34 slightly larger in diameter than the diameter of the cylindrical body portion 23 of the patellar prosthesis 10 and having a depth substantially equal or slightly less than the height of such cylindrical body portion 23. Using a reamer having a conical-shaped tip there is formed a conical-shaped section 35. The cavity 14 also includes a lower cylindrical section 36 having a diameter sized to snugly receive the post 25. Upon implantation, the patellar prosthesis 10 is positioned in an elevated position aligned with the cavity and with the spikes 32 touching the surface of the conical-shaped section 35 of such cavity at positions such that the post 25 is aligned with the lower cylindrical cavity 36. Since the patellar prosthesis of the present invention is intended to be used without cement, bone chips and/or bone meal is placed in the grooves 26 of the post 25 to promote the ingrowth of bone in those areas. The prosthesis is then forced completely into the cavity 14 with the spikes becoming embedded into the bone. As previously mentioned, the spikes are aligned such that there respective centerlines are parallel to the longitudinal axis A of the post 25 so that such spikes may be readily driven or otherwise inserted by movement of the patellar prosthesis 10 into the cavity 14 along such longitudinal axis. If the bone of the patella 9 is exceptionally hard, it may be necessary to drill small lead-in passages for each of the spikes 32.

As is well-known in the art, it is frequently necessary to replace or resection a patellar prosthesis after a number of years due to wear of the various components of the total knee system against one another. Referring now to FIGS. 4-7, there is shown a procedure for removing the patellar prosthesis as part of a resectioning operation. Initially, as shown in FIG. 4, the patellar prosthesis 10 is cut into a number of sections with four sections or quadrants 38a, 38b, 38c and 38d, being shown in FIG. 4. This cut may be performed using saws such as are well-known in the medical field which are capable of cutting the first plastic component 11 and the second metallic component 12 without damaging the patella 9 itself. One such instrument for cutting a prosthesis is one known as a Midas Rex Instrumentation System manufactured by Midas Rex Pneumatic Tools, Inc., Forth Worth, Tex. After sectioning, an instrument having a spoon shape and a cutting blade is inserted between the plastic portion 48a (See FIG. 5) of one of the sections, for example, section 38a (See FIG. 4) in order to separate it from the metallic component 58a (See FIG. 6) of such quadrant section 38a and to cut off that portion of the central stem 25 which would otherwise be connected to the portion 48a. Each of the other plastic sections 48b, 48c and 48d, is removed from the patella in a similar manner. Thereafter, the four metallic portions 58a, 58b, 58c and 58d, are removed by inserting a spoon-shaped tool between the beaded or porous portion 31 and the bone. As will be appreciated, this will require some cutting of the bone to separate it from bone which has grown into the beaded or porous portion 31.

Figure 6:
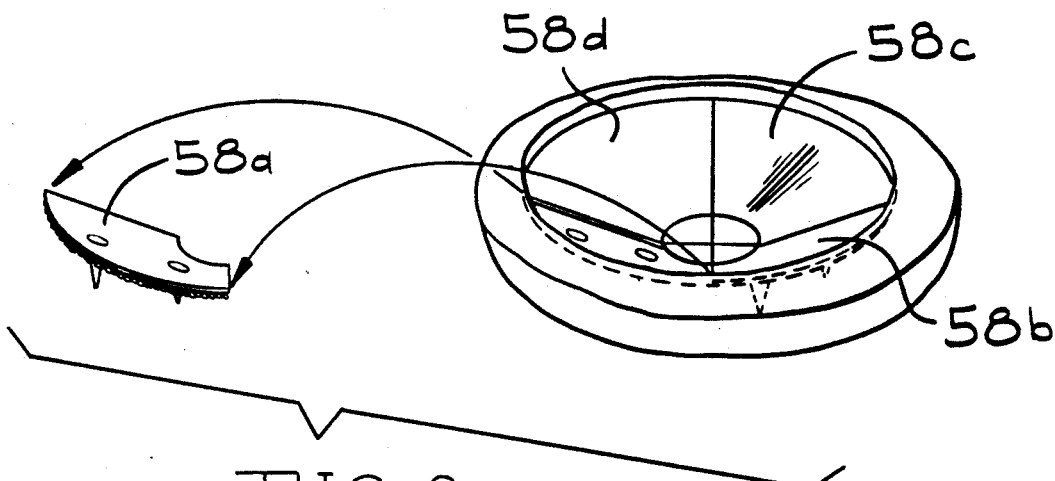
Figure 7:
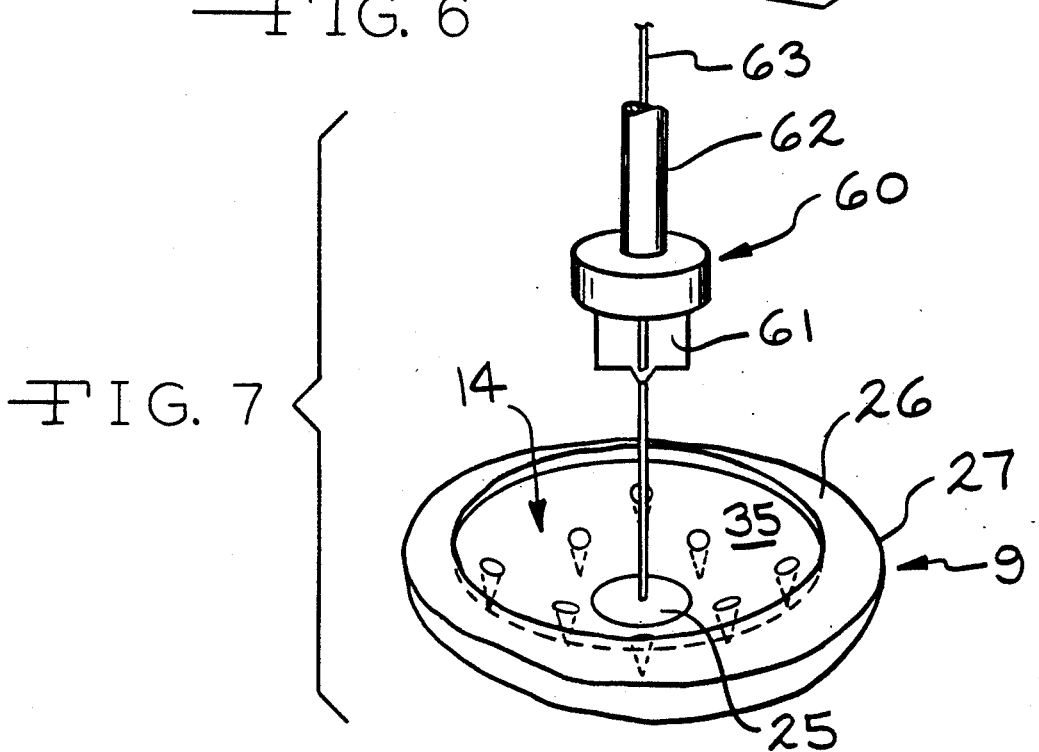

Following removal of such metallic portions 58a, 58b, 58c and 58d, as shown in FIG. 6, a reamer 60 is utilized to ream the post 25 from the lower cylindrical cavity portion 36. Preferably, the reamer 60 utilizes a cannulated blade 61 having a cannulated guide tube 62 telescoped over a guidewire 63 for accurately guiding the reamer 60 as it cuts and removes the post 25. Prior to reaming, the guidewire 63 is embedded on the longitudinal axis of the post 25.

Figure 8:
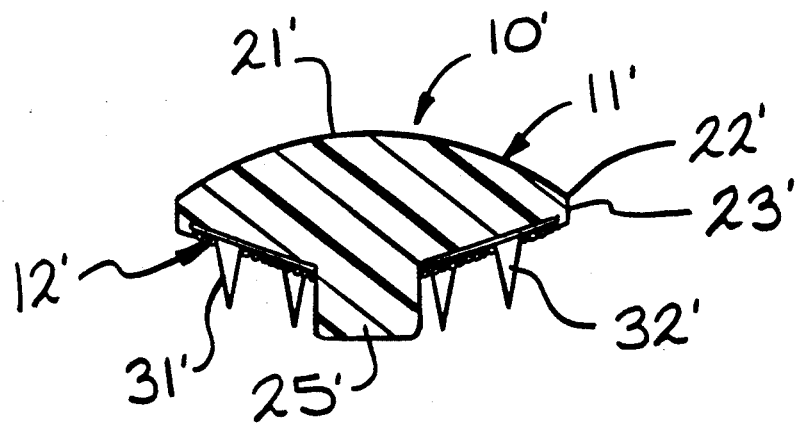
FIG. 8 is a sectional view of a modified embodiment.
Figure 9:
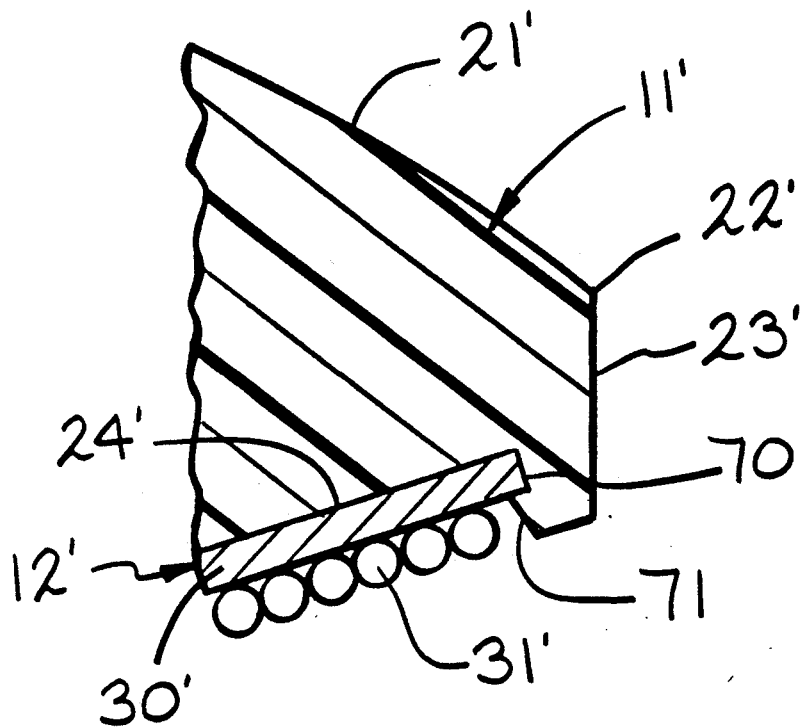
FIG. 9 is an enlarged view of a portion of the modified patellar prosthesis of FIG. 8 showing an interference fit at the periphery of the metal backing and the plastic component.

Referring now to FIGS. 8 and 9, there is shown a modified patellar prosthesis 10' having a first component 11' formed of plastic material such as a high molecular weight polyethylene and a second component 12' formed of metal such as titanium or a cobalt chrome alloy.

The first component 11' includes a dome 21' which preferably is convex throughout extending to a peripheral edge 22'. Extending downwardly from the peripheral edge 22' in a direction away from the dome 21' is a short cylindrical body section 23'. The first component 11' also has a conical-shaped surface 24' on the side opposite the dome 21' from which a central post 25' extends. The conical-shaped surface portion 24' tapers inwardly and downwardly away from a plane defined by the peripheral edge 22' as it approaches the central post 25'.

As can be seen, particularly in FIG. 9, the first component 11' is provided with a recessed portion defining an annular groove 70 defined by a lip 71 extending inwardly from the lower end of the cylindrical body section 23'. Thus, the lip 71 is spaced from and cooperates with the outer periphery of the conical-shaped surface portion 24' to define the groove 70.

The second component 12', similar to the second component 12 of the previous embodiment, is formed of metal and includes a shell 30' which snugly engages the lower conical-shaped surface portion 24' of the first component. The second metallic component 12' also has a surface of beads 31' forming a porous surface intended to receive bone ingrowth similar to the first embodiment. It also has a series of spikes 32' extending between the beads 31'.

Under this embodiment, the outer peripheral edge of the shell 30' is snapped into the groove 70 to form a freeze fit or interference fit with the first component 11'. Thus, the size of the shell 30' is such that it has a diameter slightly larger than the diameter of the inner surface of the lip 71 so that it can be retained therein. The resilience of the plastic material from which the first component 11' is manufactured permits such second metallic component 12' to be snapped over the lip 71 and into the groove 70. If necessary, the first component 11' which is formed of plastic, may be heated to more easily permit the second metallic component 12 to be snapped into the groove 70.

The patellar prosthesis of the present invention is one which provides superior performance without the necessity of utilizing bone cement to hold it in place and yet one which permits ready revision with a minimum of problems.

Many modifications will become readily apparent to those skilled in the art. Accordingly, the scope of this invention should be limited only by the scope of the appended claims.

I claim:

1. A patellar prosthesis for implantation in a prepared cavity comprising:
   (a) a first component including
      (i) a body having a central axis and an outwardly facing dome positioned for sliding engagement with a femoral prosthesis, said dome having an apex lying on said central axis, said dome extending outwardly from said central axis and terminating in a circular edge defining a plane perpendicular to said central axis, an inner surface facing away from said dome, said inner surface extending to an outer peripheral edge aligned with said circular edge, said inner surface tapering toward said plane as it approaches said outer peripheral edge; and
      (ii) post means extending from said inner surface; said post means having a plurality of grooves parallel to said central axis; and
   (b) a second component including a metal shell having
      (i) a first surface engaged to said first component inner surface substantially encircling said post means and extending outwardly therefrom; and
      (ii) a second surface facing away from said first surface and intended to engage said prepared cavity, said second surface having a porous coating for receiving bone ingrowth.

2. A patellar prosthesis according to claim 1, wherein said first component is plastic.

3. A patellar prosthesis according to claim 1, further including means for preventing rotation of said prosthesis in said prepared cavity.

4. A patellar prosthesis according to claim 3, wherein said means for preventing rotation includes a plurality of spikes extending from said second surface.

5. A patellar prosthesis according to claim 1, wherein said body inner surface has a conical configuration.

6. A patellar prosthesis according to claim 1, wherein said body includes a cylindrical portion extending from said circular edge and joining said body inner surface at said outer peripheral edge.

7. A patellar prosthesis according to claim 1, wherein said second component is frictionally engaged to said first component.

8. A patellar prosthesis comprising:
   (a) a first component including
      (i) a body having an outwardly facing convex dome positioned for sliding engagement with a femoral prosthesis, said dome extending radially outwardly and terminating in a circular edge defining a plane, said body having a central axis perpendicular to said plane, an inner surface facing away from said dome, said inner surface extending to an outer peripheral edge aligned with said circular edge; and
      (ii) post means extending from said inner surface; said post means having a plurality of grooves parallel to said central axis; and
   (b) a second component including a metal shell having
      (i) a first surface engaged to said first component inner surface substantially encircling said post means and extending outwardly therefrom; and
      (ii) a second surface facing away from said first surface and intended to engage said prepared cavity, said second surface having a porous coating for receiving bone ingrowth.

9. A patellar prosthesis according to claim 8, wherein said porous coating is spaced from said outer peripheral edge.

10. A patellar prosthesis according to claim 8 further including means for preventing rotation of said prosthesis in said prepared cavity.

11. A patellar prosthesis according to claim 8, wherein said means for preventing rotation includes a plurality of spikes extending from said second surface.

12. A patellar prosthesis according to claim 8, wherein said second surface has a conical configuration.

13. A patellar prosthesis according to claim 8, wherein said body includes a cylindrical portion extending from said circular edge and joining said body inner surface at said outer peripheral edge.

14. A patellar prosthesis according to claim 8, wherein said second component is frictionally engaged to said first component.

* * * * *